(12) United States Patent
Phipps et al.

(10) Patent No.: US 7,400,994 B2
(45) Date of Patent: Jul. 15, 2008

(54) METHOD AND TEST COMPONENT FOR ROTATABLE DISC PARTS

(75) Inventors: Anthony B Phipps, Uttoxeter (GB); Nicholas S A Cristinacce, Bristol (GB)

(73) Assignee: Rolls-Royce plc, London (GB)

( * ) Notice: Subject to any disclaimer, the term of this patent is extended or adjusted under 35 U.S.C. 154(b) by 335 days.

(21) Appl. No.: 11/220,578

(22) Filed: Sep. 8, 2005

(65) Prior Publication Data
US 2007/0239384 A1 Oct. 11, 2007

(30) Foreign Application Priority Data
Oct. 5, 2004 (GB) ................................ 0422027.3

(51) Int. Cl.
*G01L 25/00* (2006.01)
*G06G 7/48* (2006.01)

(52) U.S. Cl. ............... 702/113; 703/1; 703/2; 703/7; 702/42; 702/179

(58) Field of Classification Search ........ 703/2, 703/6, 7, 1; 702/33, 41–43, 145, 179, 108, 702/113
See application file for complete search history.

(56) References Cited

U.S. PATENT DOCUMENTS 6,102,664 A * 8/2000 Nguyen .................. 416/248
6,119,818 A 9/2000 Krumbeck

FOREIGN PATENT DOCUMENTS

SU 1 308 867 AB 3/1986

OTHER PUBLICATIONS

Cohen et al., R. Static Simulation for Deflections of a Compressor Disk by Gyroscopic Forces, Journal of the Society for Experimental Stress Analysis, SESA Spring Meeting, Apr. 1962, pp. 97-101.*

* cited by examiner

*Primary Examiner*—Russell Frejd
(74) *Attorney, Agent, or Firm*—W. Warren Taltavull; Manelli Denison & Selter PLLC

(57) ABSTRACT

Rotatable discs combined with turbine blades in engines must be tested for critical life analysis. Thus, consideration must be made as to life expectancy for such components as a result of tensile circumferential hoops as generated by the weight of blades under rotation as well as compressive axial stress as a result of thermal gradients during initial warm up. Previous testing arrangements have considered tensile circumferential hoop stress but not compressive axial stress combinations such as "Von Mises" stress. By provision of bend structures 13, 223 a bending moment is created about a base 2, 22 formed in a test component 1, 21 such that a bending moment force 4, 24 creates a bending moment in the test component 1, 21. This bending moment results in a compressive axial stress reminiscent of that in a practical turbine engine disc as a result of initial thermal gradients. In such circumstances a more realistic testing of the component 1, 21 representative of a practical disc/blade combination is achieved.

21 Claims, 1 Drawing Sheet

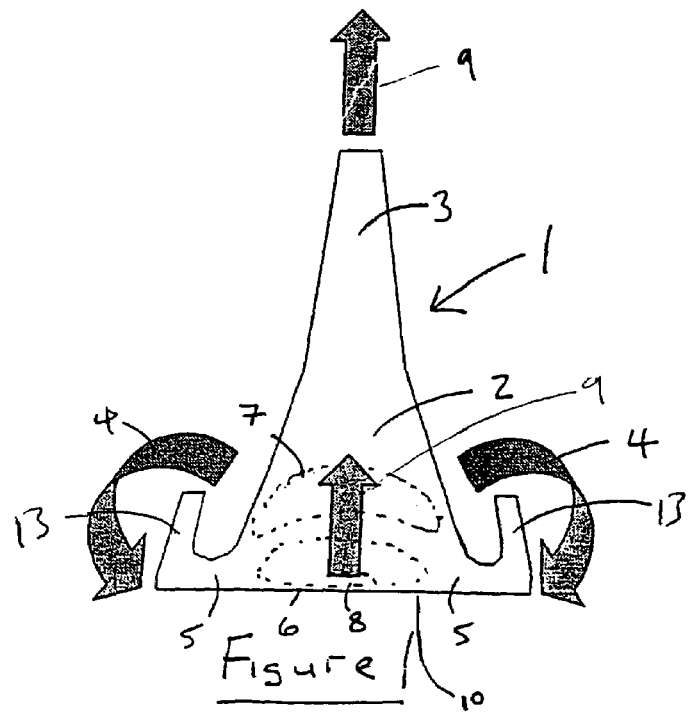
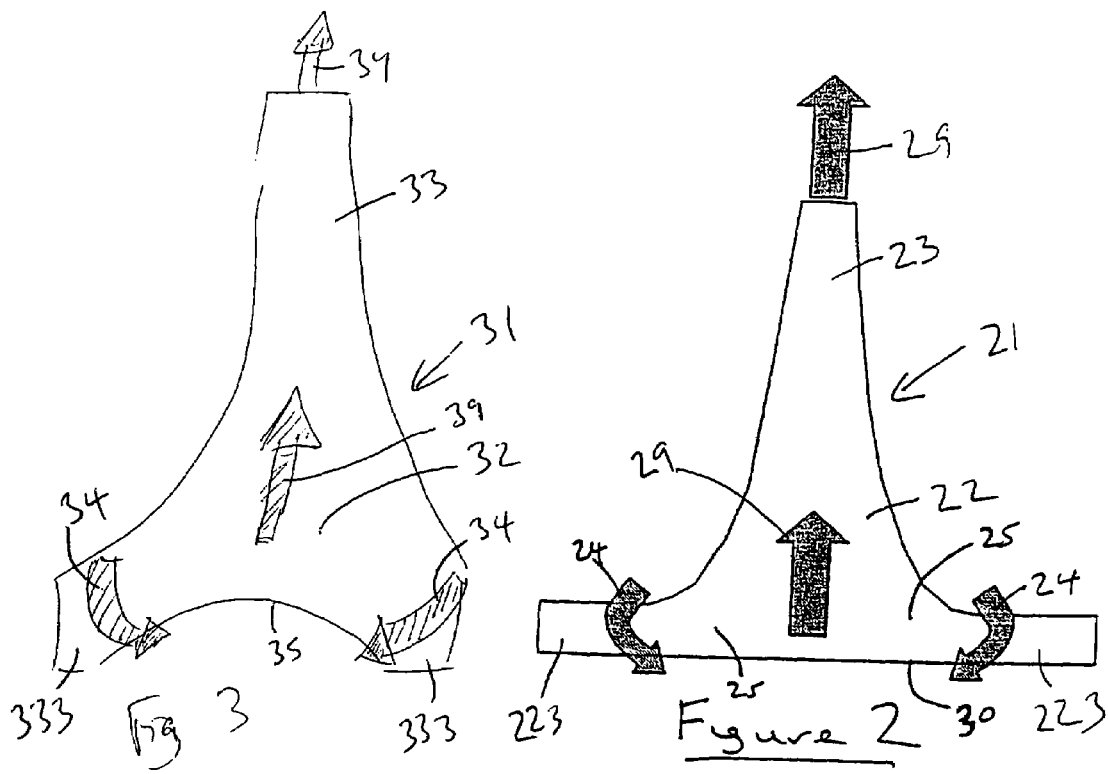

METHOD AND TEST COMPONENT FOR ROTATABLE DISC PARTS

FIELD OF THE INVENTION

The present invention relates to a method and test components used with respect to rotatable disc parts used within turbine engines and more particularly to testing of such components with respect to component life determining stresses.

BACKGROUND OF THE INVENTION

Clearly, it is necessary to ensure that components, and in particular critical components within safety and reliability driven technologies such as aircraft engines, meet necessary performance standards. Particular components within an aircraft engine which must be tested in order to determine their life expectancy within the operational environment of an engine are the turbine discs and in particular the high temperature turbine discs within a gas turbine engine. It will be understood that if such turbine discs failed in use there may be catastrophic consequences.

Unfortunately, modern turbine discs are of relatively large size with a large bore section. In such circumstances, during transient operation of an engine incorporating such turbine discs, the speed and attached blade weight to these discs can cause high (circumferential hoop) stressing to the disc upon which the blades are secured. In such circumstances it is necessary to test turbine discs and in particular the materials from which such discs are formed in order to determine expected life in an engine.

Previously, testing of turbine discs has been achieved by simple spin testing of an actual or slightly modified real engine turbine disc component. However, such an approach is undermined by the nature of large bore discs in that in operation, that is to say within an engine, the bore section takes time to heat up as a result of external heating within an operating engine. During this time the bore surface heats first whilst the centre of the bore remains relatively cool. This thermal gradient imparts a compressive axial stress on the bore that may result in erroneous test results. Generally, the compressive axial stress when added to high hoop stress due to rotation leads to a combined (Von-Mises) stress which is often far higher than the simple circumferential hoop stresses tested. In such circumstances, it is believed that the stress level tested using existing hoop stress testing techniques will give unrepresentative detected or projected operational lives compared to testing that covers the actual combination of compressive axial as well as tensile hoop stresses.

SUMMARY OF THE INVENTION

In accordance with the present invention, there is provided a method of forming and subjecting test loading upon a representative rotatable disc, the method comprising forming a test component comprising a disc extending from a base with a bend structure and applying a bending moment to said bend structure to generate a compressive axial load to simulate of external heating of the test component.

Further in accordance with the present invention, there is provided a method of testing a representative rotatable disc, the method comprising taking a test component formed and subjected to test loading as described above and simultaneously rotating that test component to apply a circumferential hoop stress load to the test component.

Additionally, in accordance with the present invention, there is provided a test component for a rotatable disc, the component comprising a representative disc extending from a base reminiscent of a rotatable disc, the base associated with a bend structure to allow variable application of bending moment to the base in order to simulate a typical compressive axial stress due to external heating of the test component.

Generally, a bend structure is provided either side of the base. Possibly, the bend structure is in the form of a hook. Alternatively, the bend structure is a lateral element. Alternatively, a bore of the disc may be shaped.

Generally, the base has a narrowing or tapering aspect broadening towards the bend structure.

Typically, the compressive axial load is provided by application of force about the junction between the base and bend structure.

BRIEF DESCRIPTION OF THE DRAWINGS

Embodiments of the present invention will now be described by way of example only with reference to the accompanying drawings in which;

FIG. 1 is a schematic cross-section of a first test component in accordance with the present invention;

FIG. 2 is a schematic cross-section of a second test component in accordance with the present invention; and FIG. 3 is a schematic cross-section of a third test component in accordance with the present invention.

DETAILED DESCRIPTION OF THE INVENTION

As with all testing arrangements, ideally the testing regime should resemble actual operating conditions to as great an extent as possible. Thus, with respect to turbine discs used in a gas turbine engine, it will be appreciated that those discs are subject to stresses induced by rotation and in particular through the weight of blades secured to the turbine discs as well as variations in environment such as temperature differentials. One particular problem is the temperature differential caused by external heating of a turbine disc, at least initially, in use and therefore ideally the effects of such temperature differentials should also be presented during testing. It will be understood that heating is from the exterior surface through to the core of the turbine disc. Thus, as indicated above, generally there will be an axial compression stress applied to the turbine disc core about that turbine discs mounting bore. In such circumstances in reality so-called "Von-Mises" stresses are created by a combination of high hoop stress loads due to disc rotation speed and attached blade weight in combination with axial compressive stress as a result of heating.

Replicating "Von-Mises" stress (circumferential hoop stress combined with compressive axial stress) is difficult without exposing the relatively large test components to similar thermal cycling to that expected with regard to an actual turbine disc. Clearly, provision of test cells of sufficient size to achieve heating similar to that expected in a practical engine is both difficult and costly.

It has been found by imparting a bending moment about a base section of a test component that it is possible to generate a compressive axial load or stress reminiscent of expected compressive axial stress due to thermal gradients imposed upon a turbine disc during engine operation. In such circumstances, in accordance with the present invention, test components are shaped such that the turbine discs under test impart a bending moment which is combined with a tensile circumferential hoop stress when the component is spun in a test rig environment. In such circumstances, the test component is better matched to in service stress levels and so better able to replicate those conditions required to achieve an accurate determination of expected turbine disc component life in use.

Referring to FIG. 1 illustrating a first test component 1 in accordance with the present invention as a schematic cross-section. Thus, the component 1 comprises a base portion 2 from which a disc representative portion 3 extends in order that the structure is similar to that of a turbine disc with blades attached as utilised in a practical engine. Either side of the base portion 2 bend structures 13 are formed. These bend structures 13 in the embodiment depicted in FIG. 1 have a hook-like cross-section such that a bending force 4 acts to create compressive axial stress in the areas marked by broken lines 6, 7 and in particular in area 8 of the bottom load defined by broken lines 6. This compressive axial stress is created by action of the bending forces 4 about pivot points located upon the junctions 5 between the bend structures 13 and the base 2.

The whole test component 1 is then subjected to tensile circumferential hoop stress 9 as a result of spinning the component 1 in a test environment.

In the above circumstances by combining the compressive axial stress 6, 7 created by the bending moment presented through the bend structures 13 along with the tensile circumferential stress 9 created by spinning the component 1, it will be understood that the actual loading placed upon the component 1 is more reflective of the conditions imposed upon an actual test turbine disc for which the test component 1 is representative and so simulates these conditions.

The compressive axial stress 6, 7 is also produced during rotation, or spinning, of the test component 1. The compressive axial stress 6, 7 is produced due to the portion 3 of the test component 1 exerting tensile, centrifugal hoop stress 9 on the base portion 2 of the test component 1 which results in radial growth, a small radial growth, of the base portion 2, whereas the bend structures 13 on both sides of the base portion 2 are not subjected to the tensile centrifugal hoop stress from the portion 3 of the test component 1 and therefore the result is a smaller radial growth of the bend structures 13 compared to the base portion 2. The difference in radial growth between the base portion 2 and the bend structures 13 produces the bending moment force 4 about the junctions 5 between the base portion 2 and bend structures 13, and hence the compressive axial stress 6, 7. The portion 3 of the test component 1 is at a greater radial distance from the axis of rotation of the test component 1 than the base portion 2 of the test component 1 and therefore the portion 3 rotates at a greater speed than the base portion 2 and is at a radius greater than the free ring radius. For radii greater than the free ring radius the test component 1 is not self supporting and for radii less than the free ring radius the test component 1 is self supporting. The base portion 2 and the bend structures 13 are positioned at radii less than the free ring radius. Thus the base portion 2 supports the portion 3 and carries the tensile centrifugal hoop stress 9 exerted on the portion 3 of the test component 1. Thus, the bend structures 13 have toroidal stiffness, but when acted upon by the centrifugally induced force, bend slightly putting the base portion 2 into axial compression.

Clearly, the actual bending moment created by bending force 4 as well as the tensile circumferential stress created by rotation will depend upon designed or predicted engine conditions. In any event, by the testing regime, a more accurate determination of actual component life will be determined to enable further refinements of the turbine disc design and/or specification for predictive surface replacement of the turbine disc in order to avoid failure in operation. Normally, a component within a turbine engine will not be operated to destruction and so through an appropriate statistically determined process, replacement of the component will be performed as a proportion of expected operational life rather than actual or predicted likelihood of failure.

FIG. 2 illustrates a second test component 21 embodiment in accordance with the present invention as a schematic cross-section. Thus, the component 21 again comprises a disc representative portion 23 extending from a base portion 22 such that upon rotation tensile centrifugal hoop stress is created in the direction of arrowheads 29 as a result of the component 21 being spun. The component 21 also includes bend structures 223 either side of the base portion 22 such that through a bending moment force 24 acting about junctions 25 between the bend structures 223 and the base portion 22 a bending moment is achieved which generates a compressive axial stress reminiscent of these thermal gradients associated with axial turbine disc operation.

The compressive axial stress is also produced during rotation, or spinning, of the test component 21. The compressive axial stress is produced due to the portion 23 of the test component 2 exerting tensile, centrifugal hoop stress 29 on the base portion 22 of the test component 21 which results in radial growth, a small radial growth, of the base portion 22, whereas the bend structures 223 on both sides of the base portion 22 are not subjected to the tensile centrifugal hoop stress 29 from the portion 23 of the test component 21 and therefore the result is a smaller radial growth of the bend structures compared to the base portion 22. The difference in radial growth between the base portion 22 and the bend structures 223 produces the bending moment force 24 about the junctions 25 between the base portion 22 and bends structures 222, and hence the compressive axial stress. The portion 23 of the test component 21 is at a greater radial distanced from the axis of rotation of the test component 21 than the base portion 22 of the test component 21 and therefore the portion 23 rotates at a greater speed than the base portion 22 and is at a radius greater than the free ring radius. For radii greater than the free ring radius the test component 21 is not self supporting and for radii less than the free ring radius the test component 21 is self supporting. The base portion 22 and the bend structures 223 are positioned at radii less than the free ring radius. Thus the base portion 22 supports the portion 23 and carries the tensile centrifugal hoop stress 29 exerted on the portion 23 of the test component 21. Thus, the bend structures 223 have toroidal stiffness, but when acted upon by the centrifugally induced force, bend slightly putting the base portion 22 into axial compression.

FIG. 3 illustrates a third representative test component 31 in accordance with the present invention as a schematic cross-section. Thus, the component again comprises a disc representative portion 33 extending from a base portion 32 such that upon rotation tensile centrifugal hoop stress is created in the direction of arrowhead 39 as a result of the component 31 being spun. The component 31 also includes bend structures 333 either side of the base portion 32. Application of a bending force 34 about the base 32 between the structures 333 and that the portion 32 ensures a bending moment is achieved which generates a compressive axial stress which simulates thermal stressing associated with actual turbine disc operation. In the embodiment depicted in FIG. 3 a bore 35 of the component 31 is shaped in order to amplify the compressive axial stress generated by rotation of the component 31. As can be seen, this generally takes the form of a curved or contoured shape, eg concave to the base 32 between the bending structures 333.

The compressive axial stress is also produced during rotation, or spinning, of the test component 31. The compressive axial stress is produced due to the portion 33 of the test component 1 exerting tensile, centrifugal hoop stress 39 on the base portion 32 of the test component 31 which results in radial growth, a small radial growth, of the base portion 32, whereas the bend structures 333 on both sides of the base portion 32 are not subjected to the tensile centrifugal hoop stress from the portion 33 of the test component 31 and therefore the result is a smaller radial growth of the bend structures compared to the base portion 32. The difference in radial growth between the base portion 32 and the bend structures 333 produces the bending moment force 34 about the junctions between the base portion 32 and bends structures, and hence the compressive axial stress. The portion 33 of the test component 31 is at a greater radial distanced from the axis of rotation of the test component 31 than the base portion 32 of the test component 31 and therefore the portion 33 rotates at a greater speed than the base portion 32 and is at a radius greater than the free ring radius. For radii greater than the free ring radius the test component 31 is not self supporting and for radii less than the free ring radius the test component 31 is self supporting. The base portion 32 and the bend structures 33 are positioned at radii less than the free ring radius. Thus the base portion 32 supports the portion 33 and carries the tensile centrifugal hoop stress 39 exerted on the portion 33 of the test component 31. Thus, the bend structures have toroidal stiffness, but when acted upon by the centrifugally induced force, bend slightly putting the base portion 32 into axial compression.

By provision of a relatively flat and lateral structure 223 it is possible to achieve differing bending moment effects in comparison with the first embodiment depicted in FIG. 1. Thus, for example shrunken firtree low expansion material rings may be added over the lateral structures 223 such that when the assembly of those rings (not shown) with the test component 21 is heated, there is the same effect to induce a compressive axial stress moment consistent with that in a practical turbine disc scenario.

By provision of both tensile circumferential stress and compressive axial stress through the application of a bending moment, it will be understood that effectively, testing is performed as if under real life component operating conditions. In such circumstances generally a test component will be specified which simulates an actual turbine disc with blades attached. Thus, the central disc portions 3, 23 depicted in FIGS. 1 and 2 will comprise as shown a loop of material extending from a bore side respectively 10, 30 in FIGS. 1 and 2. The bore will be mounted upon a test rig capable of achieving spin rotation in order to generate the tensile circumferential hoop stress typical of a practical loading upon a turbine disc in an engine. It will be understood that normally turbine blades are secured to the turbine disc through firtree or other mounting arrangements. Thus, the disc portion 3, 23 is detachable. However, with respect to a test component, the detachability of the disc portion 3, 23 may be ignored. Once the core disc has been specified, the test component in accordance with the present invention is then associated with a bend structure at least to one side in order to generate the compressive axial load typical of external thermal heating through outer surfaces of the disc/blade combination in a practical gas turbine engine. As indicated above, such bend structures 13, 223 can be altered in order to achieve the desired form of compressive axial stress in order to replicate that expected in a practical engine scenario.

In the above circumstances, the present invention describes a convenient way of simply loading a test component representative of a turbine disc/blade in order to create a compressive axial stress simulating external thermal heating upon a large component as well as overall testing of such a test component in terms of both compressive axial stress and circumferential tensile stress, a combination referred to as "Von-Mises" stress. In such circumstances, it may be possible to test the expected compressive axial stresses generated by external heating alone by applying the bending moment as described above, that is to say without rotation in order to generate the tensile circumferential stresses, but typically there are better techniques for such testing.

In designing the test component, it should be appreciated that consideration will be made to the actual weight of blades positioned upon the turbine disc in order to achieve an appropriate weight distribution for the combination in the test component in order that the correct level of tensile circumferential stress is approached, whilst similarly the test rig as well as bend structures will be chosen and specified in order to approximate the compressive axial stresses generated by external thermal heating in relation to time and/or thermal gradient. Clearly, these factors will depend upon a particular turbine disc/blade combination required for testing, but as can be seen, generally the base portions 2, 22 will have a tapered aspect broader towards the bending structure 13, 223, which reflects the nature of the centre of gravity for a practical turbine engine disc.

The test components 1, 21, 31 in accordance with the present invention will generally be of a wheel cross-section with only one side, or half shown in FIGS. 1, 2 and 3. In such circumstances, the bending moment force 4, 24, 34 will be applied to bending structures 13, 223, 333 about the whole circumference of that bending structure 13, 223, 333 to maintain the axial compressive stress throughout rotation of the component 1, 21, 31. Furthermore, the degree of axial compressive stress will be altered, generally reduced, with time in a similar fashion to equalization of temperature with time in real engine scenario.

It will be appreciated that the representative test components in accordance with the present invention may be utilised with respect to associated discs which can be used in turbine discs or compressor discs of a turbine engine. Although compressive discs notionally are not subject to hot combustion gases it would be understood that the compression of the working fluid air, that is to say such compressed air, will impart significant heating to the compressor discs which as indicated previously will then create "Von Mises" stressing. The actual discs represented by the test components may be utilised in a gas turbine engine utilised for aircraft propulsion, as a stationary industrial engine or as a marine propulsion engine. The actual discs represented by the test components may be utilised in other turbine engines or engines in which the discs are subjected to "Von Mises" stressing.

Whilst endeavoring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

We claim:

1. A method of forming and subjecting test loading upon a representative rotatable disc, the method comprising forming a test component comprising a base portion, disc portion and at least one bend structure, said disc portion extending from said base portion, the at least one bend structure being positioned at a side of the base portion, rotating said test component to simultaneously apply a circumferential hoop stress load to said test component and a bending moment to the at least one bend structure to generate a compressive axial stress in said base portion of said test component to simulate external heating of said test component.

2. A method as claimed in claim 1, wherein the disc portion extends radially from the base portion and the bend structure is at the axial side of the base portion.

3. A method as claimed in claim 1, wherein the representative rotatable disc has a bore shape so as to amplify the compressive axial stress.

4. A method as claimed in claim 1, wherein the at least one bend structure is in the form of a hook.

5. A method as claimed in claim 1, wherein the at least one bend structure is a lateral element.

6. A method as claimed in claim 1, wherein the base portion has a narrowing or tapering aspect broadening towards the at least one bend structure.

7. A method of forming and subjecting test loading upon a representative rotatable disc, the method comprising forming a test component comprising a base portion, disc portion and bend structures, said disc portion extending from said base portion, said bend structures being positioned at the sides of said base portion, rotating said test component to simultaneously apply a circumferential hoop stress load to said test component and bending moments to said bend structures to generate a compressive axial load in said base portion to simulate external heating of said test component.

8. A test component for a rotatable disc, the test component comprising a base portion, a disc portion and at least one bend structure, said disc portion extending from said base portion, the at least one bend structure being positioned at a side of said base portion to allow variable application of bending moments to said bend structure to simulate a compressive axial stress in said base portion due to external heating of the test component.

9. A test component as claimed in claim 8, wherein the disc portion extends radially from the base portion and the bend structure is at the axial side of the base portion.

10. A test component as claimed in claim 8, wherein the at least one bend structure is in the form of a hook.

11. A test component as claimed in claim 8, wherein the at least one bend structure is a lateral element.

12. A test component as claimed in claim 8, wherein the base portion has a narrowing or tapering aspect broadening towards the at least one bend structure.

13. A test component as claimed in claim 8, wherein the compressive axial stress is provided by application of force about the junction between the base portion and the at least one bend structure.

14. A test component as claimed in claim 8, wherein the rotatable disc has a bore shaped so as to amplify the compressive axial stress.

15. A test component for a rotatable disc, the test component comprising a base portion, a disc portion and bend structures, said disc portion extending from said base portion, said bend structures being positioned at the sides of said base portion to allow variable application of bending moments to said bend structures to simulate a compressive axial stress in said base portion due to external heating of said test component.

16. A method as claimed in claim 15, wherein the compressive axial stress is provided by generation of force about the junction between the base and bend structure as the component rotates.

17. A method of forming and subjecting test loading upon a representative rotatable disc, the method comprising forming a test component comprising a disc portion extending from a base portion with at least one bend structure and applying a bending moment to the at least one bend structure to generate a compressive axial stress to simulate external heating of the test component wherein the representative disc has a bore shape so as to amplify the compressive axial stress.

18. A test component for a rotatable disc, the test component comprising a representative disc portion extending from a base portion reminiscent of a rotatable disc, the base portion associated with a bend structure to allow variable application of bending moment to the base portion in order to simulate a typical compressive axial stress due to external heating of the test component wherein the bend structure is provided on either side of the base portion.

19. A test component as claimed in claim 18, wherein the bend structure is in the form of a hook.

20. A test component as claimed in claim 18, wherein the bend structure is a lateral element.

21. A test component as claimed in claim 18, wherein the representative disc has a bore shaped so as to amplify the compressive axial stress.

* * * * *